(12) United States Patent
Walton et al.

(10) Patent No.: US 12,220,115 B2
(45) Date of Patent: Feb. 11, 2025

(54) REPAIR OR REFURBISHMENT OF LIMITED USE MEDICAL DEVICES

(71) Applicant: Medline Industries, LP, Northfield, IL (US)

(72) Inventors: Richard Walton, North Andover, MA (US); Harold D. Pogue, Framingham, MA (US); Richard L. McCulley, Jr., Weymouth, MA (US); James Patrick Wiggins, Redmond, OR (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 18/136,227

(22) Filed: Apr. 18, 2023

(65) Prior Publication Data

US 2023/0248341 A1    Aug. 10, 2023

Related U.S. Application Data

(60) Division of application No. 17/372,223, filed on Jul. 9, 2021, now Pat. No. 11,647,996, which is a
(Continued)

(51) Int. Cl.
| | |
|---|---|
| *A61B 17/00* | (2006.01) |
| *A61B 18/14* | (2006.01) |
| *H01R 13/66* | (2006.01) |
| *H01R 13/68* | (2011.01) |
| *H01R 43/20* | (2006.01) |
| *H05K 7/02* | (2006.01) |
| *A61B 18/00* | (2006.01) |
| *A61B 90/00* | (2016.01) |

(52) U.S. Cl.
CPC .......... *A61B 17/00* (2013.01); *A61B 18/1402* (2013.01); *H01R 13/665* (2013.01); *H01R 13/68* (2013.01); *H01R 43/205* (2013.01); *H05K 7/02* (2013.01); *A61B 2017/00225* (2013.01); *A61B 2018/00601* (2013.01); *A61B 2018/00988* (2013.01); *A61B 2090/0803* (2016.02); *A61B 2090/0813* (2016.02); *Y10T 29/49004* (2015.01); *Y10T 29/49718* (2015.01); *Y10T 29/53174* (2015.01)

(58) Field of Classification Search
CPC ............... A61B 17/00; Y10T 29/49004; Y10T 29/49002; Y10T 29/49718; Y10T 29/53174; H05K 7/02; H05K 3/225; H05K 3/30; Y10S 323/911
USPC .. 29/593, 402.01, 402.09, 402.14, 729, 739, 29/745, 787, 825, 829, 831, 854
See application file for complete search history.

(56) References Cited

U.S. PATENT DOCUMENTS

| | | |
|---|---|---|
| 4,897,789 A | 1/1990 | King et al. |
| 5,162,725 A | 11/1992 | Hodson et al. |

(Continued)

*Primary Examiner* — Thiem D Phan
(74) *Attorney, Agent, or Firm* — SandBright, PLLC; Robert Dan Spendlove

(57) ABSTRACT

A powered medical device includes electronic components on a circuit board embedded within the body of a plug for connecting the device with a control apparatus. The medical device may be repaired or refurbished without the need to access the embedded circuit board through the use of a supplemental circuit board installed into the open end of the plug adjacent the plug pins. The supplemental circuit board may include a variety of electronic components, including fuses or non-volatile memory.

19 Claims, 10 Drawing Sheets

Related U.S. Application Data continuation of application No. 16/437,216, filed on Jun. 11, 2019, now Pat. No. 11,083,442, which is a division of application No. 15/432,985, filed on Feb. 15, 2017, now Pat. No. 10,321,899, which is a continuation of application No. 14/843,404, filed on Sep. 2, 2015, now Pat. No. 9,578,773.

(56) References Cited

U.S. PATENT DOCUMENTS

| | | | |
|---|---|---|---|
| 5,312,453 A * | 5/1994 | Shelton | A61N 1/36514 607/19 |
| 5,400,267 A * | 3/1995 | Denen | H02J 3/00 323/911 |
| 6,165,173 A | 12/2000 | Kamdar et al. | |
| 6,237,604 B1 | 5/2001 | Burnside et al. | |
| 6,308,089 B1 | 10/2001 | Ruhr et al. | |
| 6,387,092 B1 | 5/2002 | Burnside et al. | |
| 6,480,762 B1 | 11/2002 | Uchikubo et al. | |
| 6,537,272 B2 | 3/2003 | Christopherson et al. | |
| 6,578,579 B2 | 6/2003 | Burnside et al. | |
| 6,849,074 B2 | 2/2005 | Chen et al. | |
| 6,975,968 B2 | 12/2005 | Nakamitsu et al. | |
| 7,035,762 B2 | 4/2006 | Menard et al. | |
| 7,048,687 B1 | 5/2006 | Reuss et al. | |
| 7,118,564 B2 | 10/2006 | Ritchie et al. | |
| 7,149,773 B2 * | 12/2006 | Haller | G16H 40/40 607/9 |
| 7,241,270 B2 | 7/2007 | Horzewski et al. | |
| 7,261,709 B2 | 8/2007 | Swoyer et al. | |
| 7,261,710 B2 | 8/2007 | Elmouelhi et al. | |
| 7,335,197 B2 | 2/2008 | Sage et al. | |
| 7,465,301 B2 | 12/2008 | Bek et al. | |
| 7,479,019 B2 | 1/2009 | Kent et al. | |
| 7,937,163 B2 | 5/2011 | Sekiguchi | |
| 2009/0065565 A1 | 3/2009 | Cao | |
| 2010/0280511 A1 | 11/2010 | Rachlin et al. | |
| 2014/0060161 A1 | 3/2014 | Schick et al. | |

* cited by examiner

REPAIR OR REFURBISHMENT OF LIMITED USE MEDICAL DEVICES

RELATED APPLICATIONS

This application is a divisional application of U.S. patent application Ser. No. 17/372,223 filed on Jul. 9, 2021, which application is a continuation of U.S. patent application Ser. No. 16/437,216 filed on Jun. 11, 2019, now U.S. Pat. No. 11,083,442 issued Aug. 10, 2021, which application is a divisional application of U.S. patent application Ser. No. 15/432,985 filed on Feb. 15, 2017, now U.S. Pat. No. 10,321,899 issued Jun. 18, 2019, which application is a continuation of U.S. patent application Ser. No. 14/843,404 filed on Sep. 2, 2015, now U.S. Pat. No. 9,578,773 issued Feb. 21, 2017.

BACKGROUND

The present invention is directed to powered medical devices. In particular, the present invention relates to the repair and refurbishment of such powered medical devices.

Endoscopy in the medical field allows internal features of the body of a patient to be viewed without the use of traditional, fully invasive surgery. Endoscopic imaging systems enable a user to view a surgical site and endoscopic cutting instruments enable non-invasive surgery at the site.

Powered medical devices, including electrosurgical instruments, have been used together with endoscopy to cut and shape tissue at the surgical sites to which these instruments are applied. A typical electrosurgical instrument has an elongated shaft, sometimes called a "probe," with a handle at one end and a tip at the opposed end. One type of electrosurgical instrument available to surgeons is referred to as a bipolar electrosurgical instrument. An active electrode is fitted into the tip of this instrument. The shaft of the bipolar electrosurgical instrument functions as the return or reference electrode. A generator provides energy to a distal end tip of a probe within the surgical site. In one mode, the probe provides energy at a power level to ablate or otherwise surgically remove tissue. In another instance, energy is provided to the probe in order to coagulate the tissue at the surgical site to minimize bleeding thereat.

Tissue ablation is achieved when a high power electrical signal having a sufficiently large voltage is generated by a control console and directed to an attached probe. Application of the high power signal to the probe results in a large voltage difference between the two electrodes located at the tip of the probe (presuming a bipolar probe). This large voltage difference leads to the formation of an ionized region between the two electrodes, establishing a high energy field at the tip of the probe. Applying the tip of the probe to organic tissue leads to a rapid rise in the internal temperature of the cells making up the neighboring tissue. This rapid rise in temperature near instantaneously causes the intracellular water to boil and the cells to burst and vaporize, a process otherwise known as tissue ablation. An electrosurgical "cut" is thus made by the path of disrupted cells that are ablated by the extremely hot, high energy ionized region maintained at the tip of the probe. An added benefit of electrosurgical cuts is that they cause relatively little bleeding, which is the result of dissipation of heat to the tissue at the margins of the cut that produces a zone of coagulation along the cut edge.

In contrast to tissue ablation, the application of a low power electrical signal having a relatively low voltage to the active electrode located at the tip of the probe results in coagulation. Specifically, the lower voltage difference established between the active and return electrodes results in a relatively slow heating of the cells, which in turn causes desiccation or dehydration of the tissue without causing the cells to burst.

The electrosurgical instruments described above and many other medical devices, both therapeutic and diagnostic, are electrically powered and include electrically powered control or sensing means. These devices may have only a limited useful life before repair or refurbishment is necessary. The limited lifetime of these devices is determined as the period during which the devices can be relied upon to perform well, after which the devices must either be replaced or serviced. Examples of limited-use therapeutic devices are electrosurgical operating instruments such as electrocautery surgical diathermies and hemostatic scalpels, endoscopic devices such as laparoscopic scissors and probes, arthroscopic operating instruments, angioplasty reaming instruments, and ultrasonic instruments. Examples of limited-use diagnostic devices are physiologic sensors, such as those used for the measurement or monitoring of physiological and biochemical parameters, (i.e. oxygen, glucose, etc.).

Accordingly, methods have been developed for accurately tracking the usage of a limited-use medical device. The ability to track device usage provides the capability for replacing or refurbishing a device before it fails, a vital consideration where the device is used in critical medical applications, such as surgical operations, or monitoring critically ill patients.

For example, powered medical devices may include a non-volatile memory device for tracking and accumulating usage data. In addition, a non-volatile memory device associated with a limited-use medical device may be used to automatically set the operational parameters (or other parametric data) for the limited-use device when the device is connected to a generator or other power supply, controller or measuring apparatus.

Alternatively, powered medical devices may include other electronic components that identify the medical device and indicate that the medical device has previously been used. For example, medical devices use one or more resistors that identify the medical device type when it is attached to a generator and one or more fuses that are selectively blown to indicate that the device has been used.

In certain powered medical devices, the non-volatile memory or other electronic components may be encapsulated inside a plug of the device. This configuration has several advantages, including compact size and increased protection for the electronic components. However, this arrangement also prevents the electronic components from being accessed for repair or refurbishment without cutting open or otherwise damaging the plug and destroying its integrity and usefulness.

Accordingly, a need exists for a method that allows repair or refurbishment of electronic components within the plug of a powered medical device without damaging the plug.

BRIEF DESCRIPTION OF THE DRAWINGS

The foregoing and other advantages of the invention will become apparent upon reading the following detailed description and upon reference to the drawings.

Figure 1:
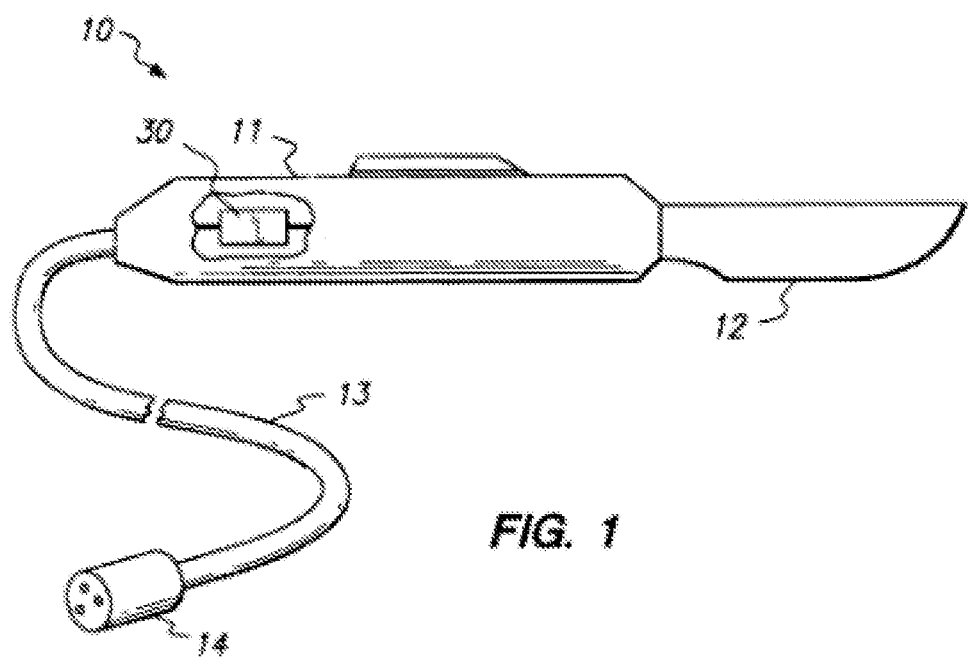
FIG. 1 shows a side view of an electrically powered medical device in accordance with embodiments of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions. Also, reference designators shown herein in parenthesis indicate components shown in a figure other than the one in discussion. For example, talking about a device (10) while discussing figure A would refer to an element, 10, that is not shown in figure A but is shown in a different figure.

Referring to FIG. 1, an illustrative embodiment of an electrically powered medical device having electronic components, such as resistors, fuses or non-volatile memory, encapsulated in a connector is described. Device 10 comprises an electrically powered scalpel having handle 11, blade 12, cable 13, and connector 14. Device 10 is merely one illustration of an electrically powered medical device, and those skilled in the art will immediately recognize applicability of the present invention to a vast array of electrically powered medical devices. Electrical cable 13 terminates at connector 14, which connects device 10 to an external power supply and control apparatus. Electronic components 30 may be disposed within connector 14 of device 10. The present invention may also be practiced with an instrument having handle 11, so that the electronic components are disposed within the handle.

Figure 2:
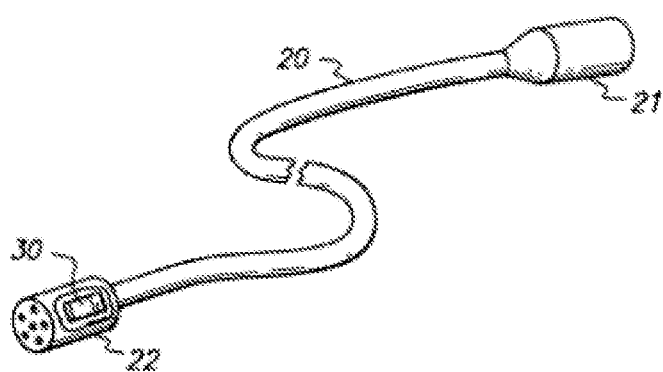
FIG. 2 shows, partly in section, an embodiment of a detachable electrical connecting cable for use with an electrically powered medical device.

FIG. 2 depicts a connecting cable 20, which may be used interchangeably with a number of compatible medical instruments. Connecting cable 20 terminates at each end with electrical connectors 21 and 22. Electronic components 30 may be disposed within either electrical connector 21 or 22 to store data or provide other functionality pertaining to use of the cable.

In an embodiment of the invention, a powered medical device includes a plug or connector that attaches and electrically connects the medical device with a generator.

Figure 3:
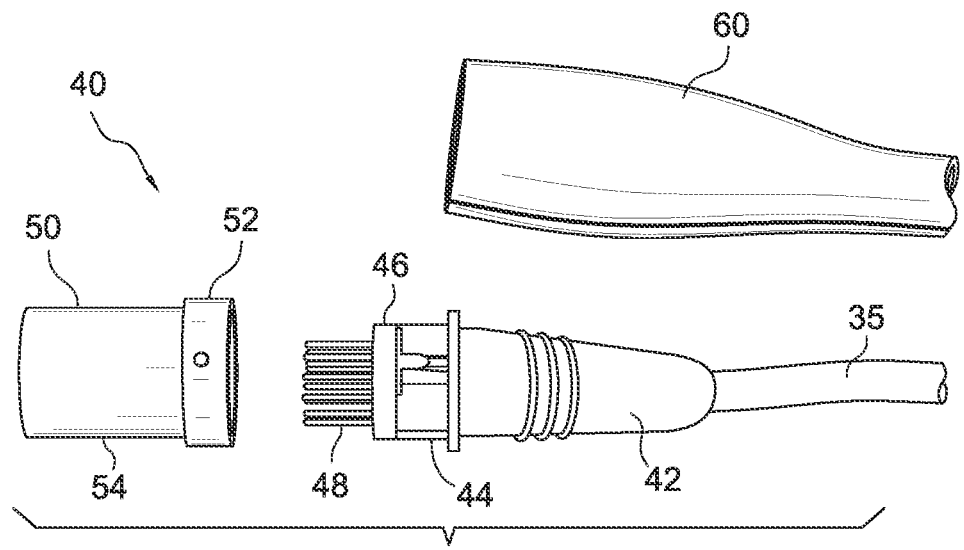
FIG. 3 shows an exploded view of an embodiment of a plug intended for use with a powered medical device.

FIG. 3 shows an exploded view of an embodiment of a plug intended for use with a powered medical device. As illustrated in FIG. 3, the plug 40 connects with a cable 35. The cable may include one or more wire strands surrounded by a shielding material. The cable connects the powered medical device to a generator or other control or measurement apparatus designed to provide power to the powered medical device.

The cable 35 passes into a protective element 42. Inside the protective element 42, the shielding material ends and the individual wires are separated to a greater degree. The protective element 42 may be formed of a rigid or flexible material and encompasses the wires. A hub 44 abuts the protective element. The hub may be formed of a rigid material, in particular a thermoplastic or thermoset polymer material. A circuit board 46 is positioned adjacent a forward surface of the hub 44 opposite the protective element 42. A plurality of pins 48 protrudes from a forward surface of the circuit board 46. Embodiments of the plug further include a shield 50. A rearward portion 52 of the shield surrounds a portion of the hub 44 and the circuit board 46. A hollow forward portion 54 of the shield extends forward from the circuit board and surrounds the pins 48, protecting the pins from damage during use. Alternatively, the plug may use bars, pads, rings or other connectors that electrically connect the plug 40 with the cable 35.

Figure 6:
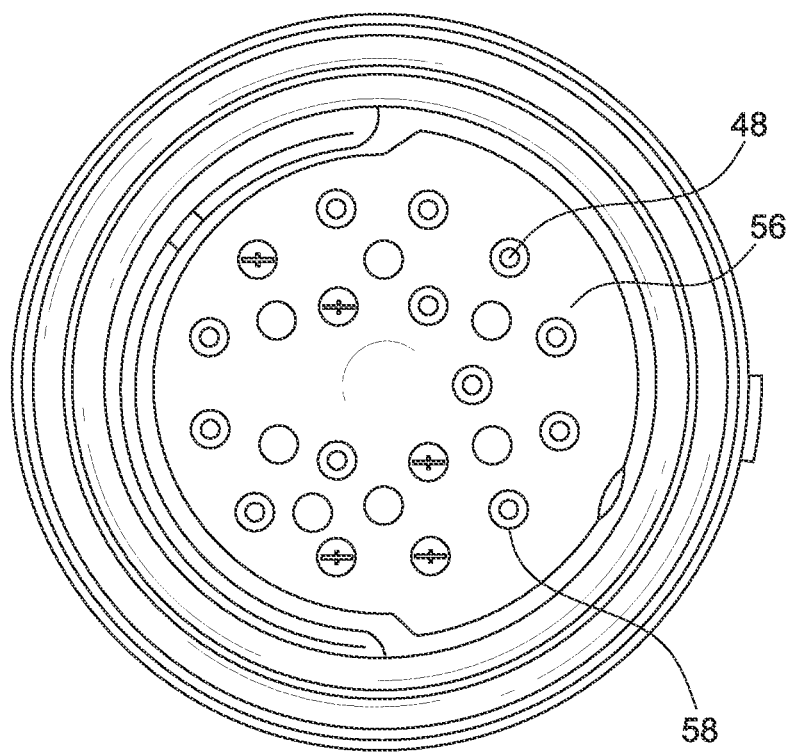
FIG. 6 shows a view from a forward end of a plug in accordance with FIG. 5.

A dividing member 56 (see FIG. 6) may extend across the inside of the shield 50 between the rearward 52 and forward 56 portions of the shield. The dividing member may have through holes 58 that accommodate pins 48 extending forward from the circuit board 46. The dividing member 56 may be integrally formed with the shield 50, for example, by injection molding. Alternatively, the dividing member may be formed separately from and inserted into the shield.

The plug 40 may also include a sheath 60. The sheath wraps around at least a portion of the cable 35, protective element 42 and hub 44. The sheath may continue forward, encompassing the circuit board 46 and at least a portion of the shield 50. In this manner, the circuit board 46 is encapsulated within the plug 40 and is only accessible by cutting apart or otherwise destroying one or more elements of the plug.

Figure 5:
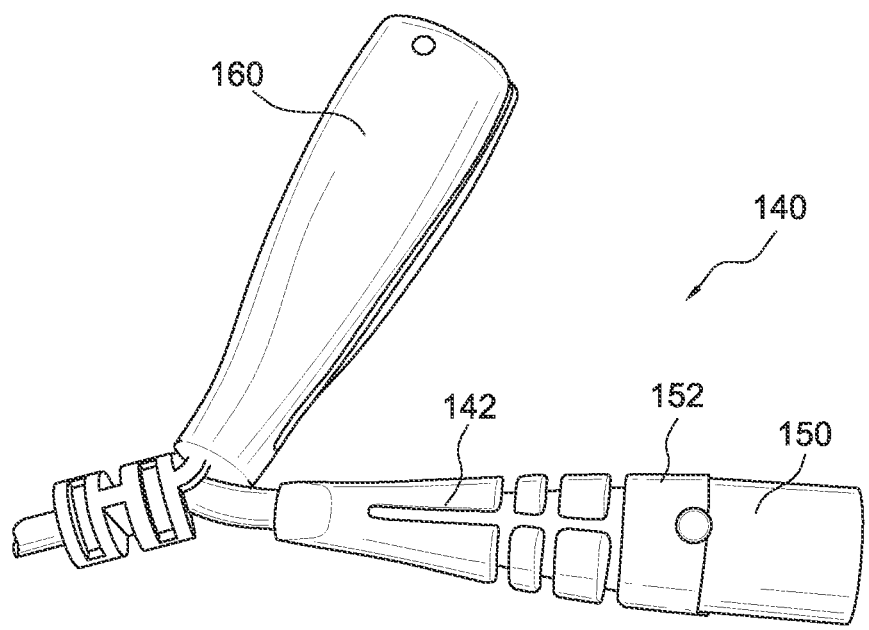
FIG. 5 shows an alternative embodiment of a plug intended for use with a powered medical device.

FIG. 5 shows an alternative embodiment of a plug 140 that does not make use of a hub. A circuit board (not shown) is placed adjacent a rearward end of a shield 150. A protective element 142 extends around the circuit board and over a rearward portion 152 of the shield. A sheath 160 encompasses the protective element 142.

Figure 4:
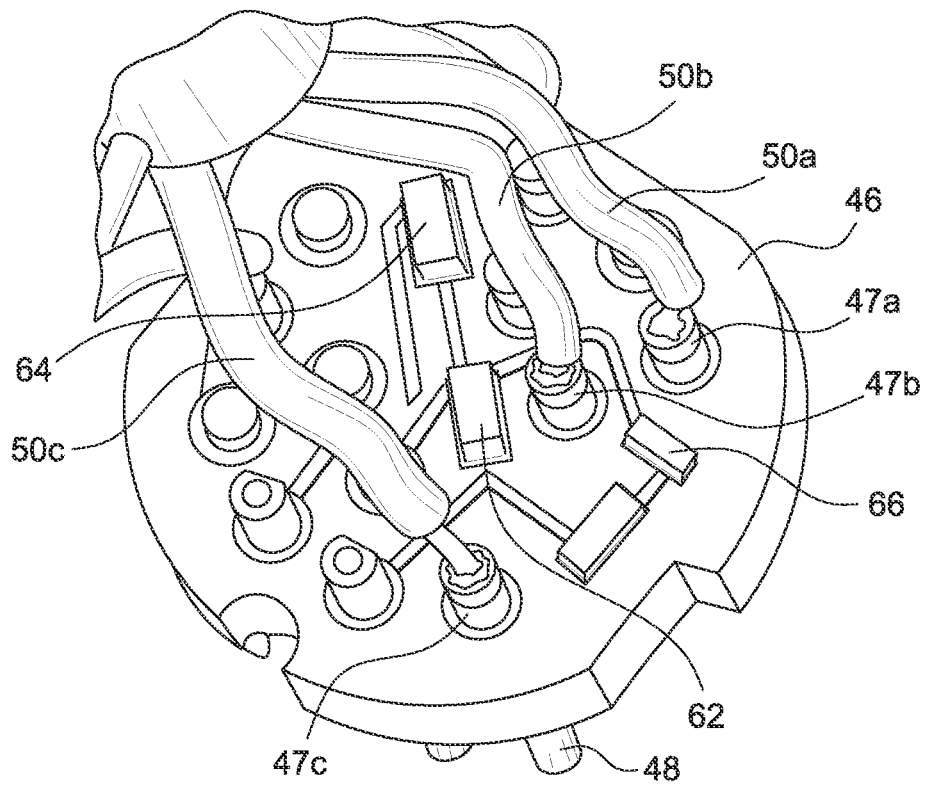
FIG. 4 shows an embodiment of a circuit board in accordance with an embodiment of the present invention.

FIG. 4 shows an embodiment of a circuit board 46 as used in the plug 40. The figure illustrates the rearward side of the circuit board. Individual wires 50a, 50b, 50c connect to rearward ends 47a, 47b, 47c of pins 48 respectively. The pins 48 extend forwardly through the circuit board and out into the hollow forward portion of the shield 54 so that the pins can be used to engage the generator. The illustrative embodiment of FIG. 4 includes first and second resistors 62, 64 mounted to the circuit board 46. When the powered medical device, which may be referred to as a "wand," is connected to the generator, these resistors serve to identify the wand type and power limits for the generator.

The circuit board also includes a fuse 66 that bridges one of the resistors 62. When the wand is used in conjunction with a generator, this fuse-bridged resistor 62 is checked. If the fuse 66 is intact, the generator sends a power pulse to blow the fuse. Control circuitry in the generator then allows use of the wand for a limited period of time. During this period, the wand can be disconnected and reconnected without error on the generator. In a further embodiment, another wand of the same model may be hooked up to the generator and used as the original one during the limited time period. If, at any point within the limited time period, the generator is switched off or loses power, the wand will no longer function. If the fuse is detected as blown, the generator may display an error code and prevent use of the wand.

Accordingly, the fuse 66 may be blown and the usage time of the wand may be limited to the designated period of time. However, it is possible that the usage time may be unintentionally reduced below the designated period of time if the generator is turned off, or if the fuse is unintentionally blown or damage. In either event, there is no way to access the fuse in order to repair or refurbish the fuse without destroying the plug.

Figure 7:
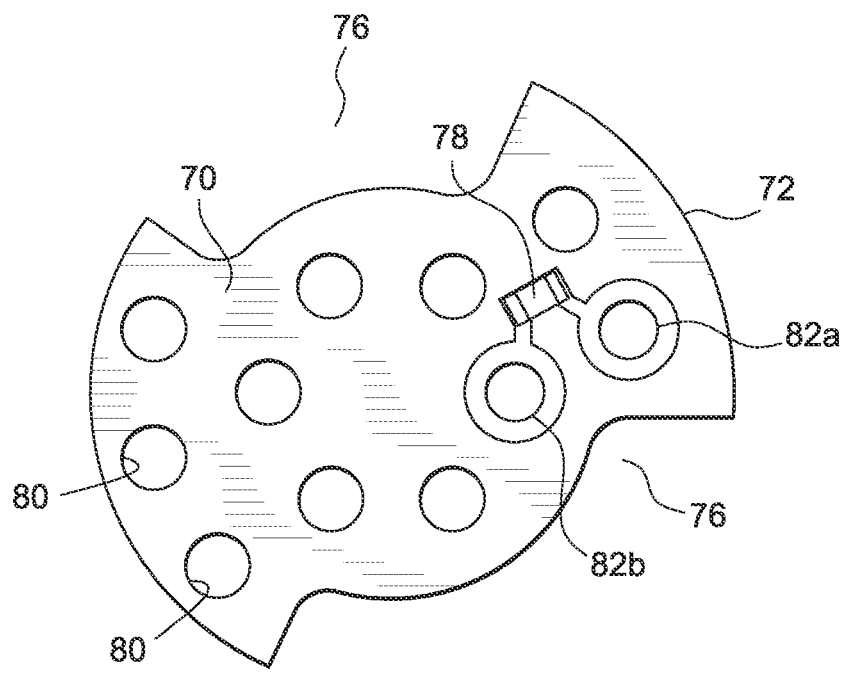
FIG. 7 shows a plan view of a supplemental circuit board in accordance with embodiments of the present invention.
Figure 8:
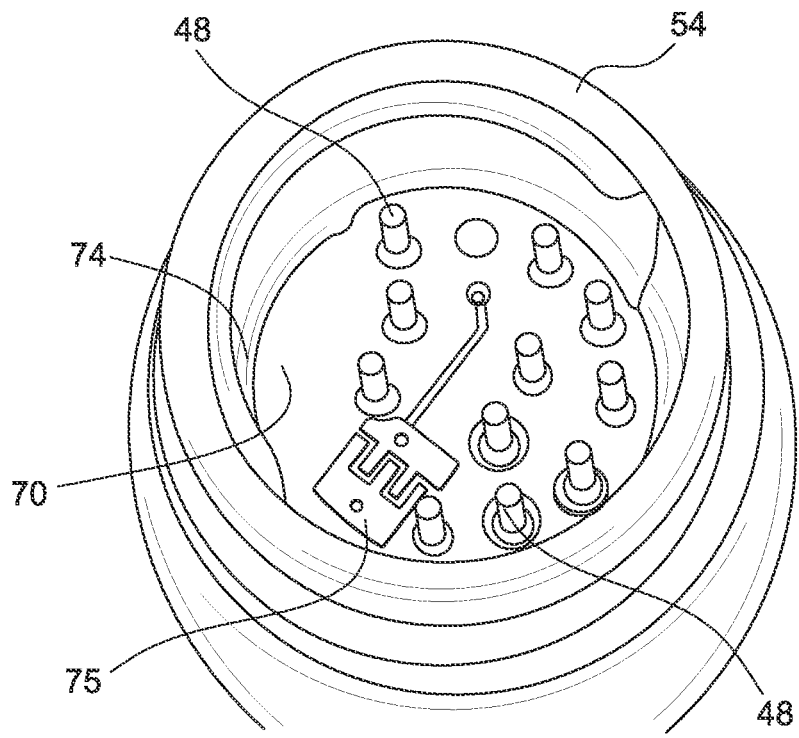
FIG. 8 shows a view of a forward end of a plug as illustrated in FIG. 6 with a supplemental circuit board installed.

In accordance with embodiments of the invention, as illustrated in FIGS. 7-8, a supplemental circuit board 70 is provided. An embodiment of the supplemental circuit board 70 has a periphery 72 that generally matches the geometry of the inside edge 74 of the forward part of the shield 54. The supplemental circuit board 70 also includes one or more cutout portions 76. These cutouts allow for removal of the circuit board as will be discussed below. The supplemental circuit board carries a fuse 78 and includes holes 80 in the circuit board that allow the pins 48 to pass through. The supplemental circuit board is inserted into the forward portion 54 of the shield 50 such that it sits at the base of the pins 48, adjacent to the dividing member 56 of the shield.

The holes 82a, 82b of the supplemental circuit board 70 that correspond to the pins that are connected by the fuse 66 on the circuit board 46 are connected via the fuse 78 on the supplemental circuit board. These holes 82a, 82b are sized such that they are biased to contact the pins with a friction fit and provide an electrical contact between the fuse 78 and the pins. Alternatively, these pins could be soldered to contact patches formed on the circuit board, soldered to other elements of the circuit board, adhered with a conductive adhesive, or connected by other means known to those of skill in the art.

Figure 10:
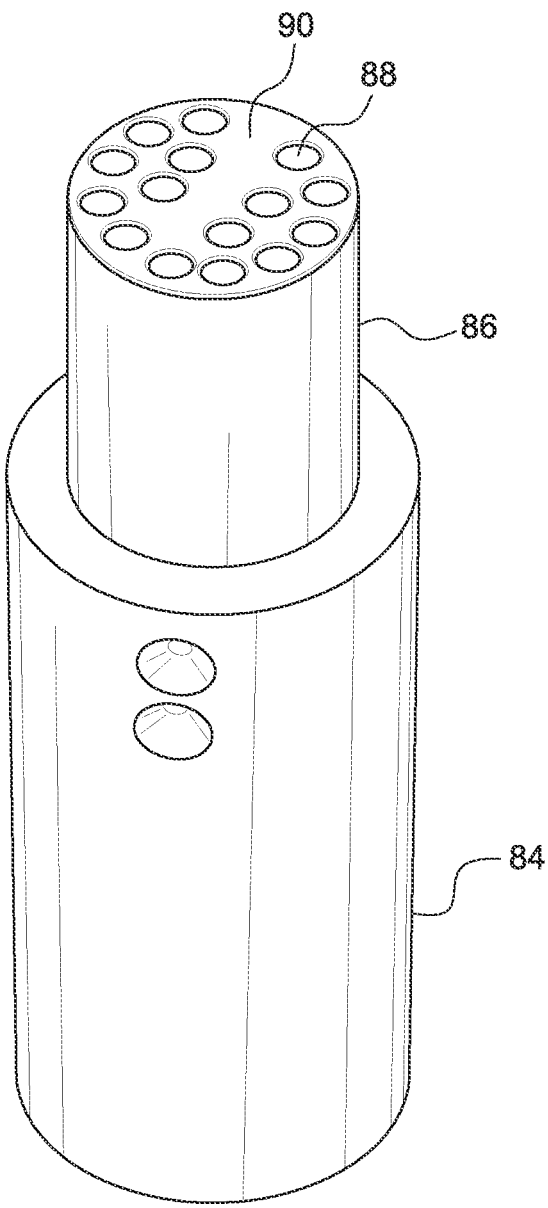
FIG. 10 shows an isometric view of an installation tool in accordance with embodiments of the present invention.

The supplemental circuit board 70 is placed into the open end of the shield 54 and is pressed into position against the dividing member 56 using an installation tool 84, as illustrated in FIG. 10. The installation tool 84 has a plunger end 86 that includes holes 88 that correspond with the pins 48 of the plug 40. The geometry of periphery of the plunger end matches the inside geometry of the plug shield open end 54. During repair or refurbishment of a powered medical device or wand, the supplemental circuit board 70 is placed on the top surface 90 of the plunger end 86 of the installation tool 84. The supplemental circuit board is shaped such that it only fits on the insertion tool in one orientation.

The supplemental circuit board is held in place on the insertion tool top surface by vacuum. The installation tool 84, with the supplemental circuit board 70 held on the top surface, is inserted into the plug. The contact force between pins 48 and one or more holes 80, 82a, 82b in the supplemental circuit board holds the supplemental circuit board in place within the plug and the installation tool is removed, leaving the supplemental circuit board positioned in the open end of the plug against the base of pins 48. The fuse 78 of the supplemental circuit board is functionally equivalent to the fuse 66 of the circuit board 46. This means that the fuse 78 functions in a sufficiently similar manner such that the powered medical device is capable of functioning with the fuse 78 used in place of the fuse 66. In this manner, a fuse that was burned or otherwise damaged as part of the time limiting function of the powered medical device may be replaced without the need to replace the entire plug or damage the integrity of the plug by destroying a plug component to gain access to the fuse.

Figure 9:
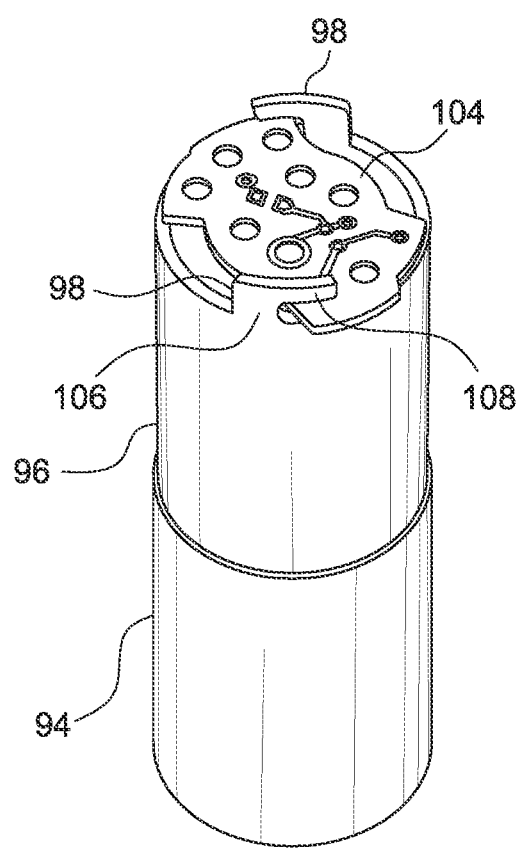
FIG. 9 shows an isometric view of a removal tool in accordance with embodiments of the present invention.

In embodiments of the invention, the supplemental circuit board 70 may be removed and replaced with a second supplemental circuit board so that the wand may be repaired or refurbished more than once. The supplemental circuit board includes cutout sections 76 along a periphery 72 of the board. These cutouts 76 extend at least some distance into the surface of the board 70. As shown in FIG. 9, a removal tool is provided. The removal tool 94 includes a forward section 96 that is smaller in diameter than the inside of the forward portion of the shield 54. Prongs 98 extend from a top surface 104 of the removal tool. The prongs consist of a base section 106 that extends upward from the top surface of the removal tool and an engagement section 108 that extends laterally from the base section.

Figure 11:
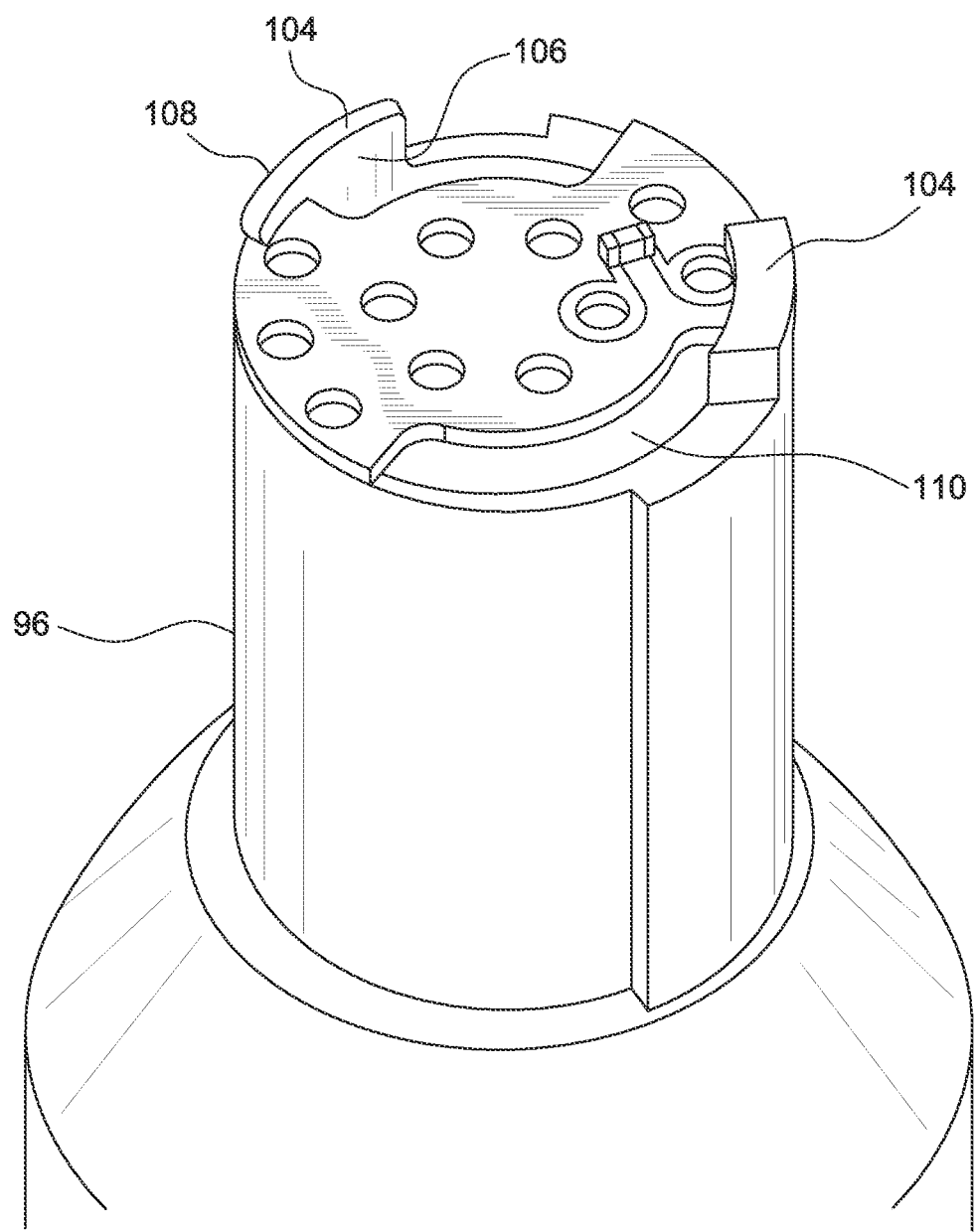
FIG. 11 shows an embodiment of a removal tool as illustrated in FIG. 9 engaging a supplemental circuit board.

To remove a supplemental circuit board 70 from a plug 40, the removal tool is inserted into the open end 54 of the plug such that the prongs 104 align with the cutouts 76 in the circuit board. The removal tool is then twisted such that the engagement portion 108 of the prongs 104 slides beneath a bottom surface of the circuit board 70 as shown in FIG. 11. The removal tool may then be pulled away from the plug, thereby removing the supplemental circuit board. The removal tool 96 may include a hollow interior portion 110 that surrounds the pins 48 and allows the removal tool to be inserted and rotate without interfering with the pins. In alternative embodiments, the supplemental circuit board may be sufficiently thin to allow multiple supplemental circuit boards to be installed one on top of the other such that it would not be necessary to remove a previous supplemental circuit board in order to repair or refurbish the wand more than once.

In an alternative embodiment, as illustrated in FIG. 8, the supplemental circuit board 70 may have two connected fuses (not shown). The first fuse is connected with the relevant pins 48 as discussed with respect to FIG. 7. The second fuse is connected between the pins with a shorting pad 75 placed in series with the fuse. In this manner, the supplemental circuit board may be installed and used with the wand a first time. When the first fuse has been blown, the supplemental circuit board may be used a second time by connecting the elements of the shorting pad using conductive ink or other appropriate means to bridge the elements thereby connecting the second fuse between the pins.

In further embodiments of the invention, the circuit board of the plug 40 may include non-volatile memory that stores one or more parameters relating to the wand type or function. For example, the non-volatile memory may include information that is provided to the generator in order to properly control the wand. The non-volatile memory may also include information indicating wand activation time and/or usage time. In this manner, the generator may determine how long the wand has been used and limit use of the wand to a certain period of time. However, as discussed above, the wand may not be repaired or refurbished without destroying the plug.

Figure 12:
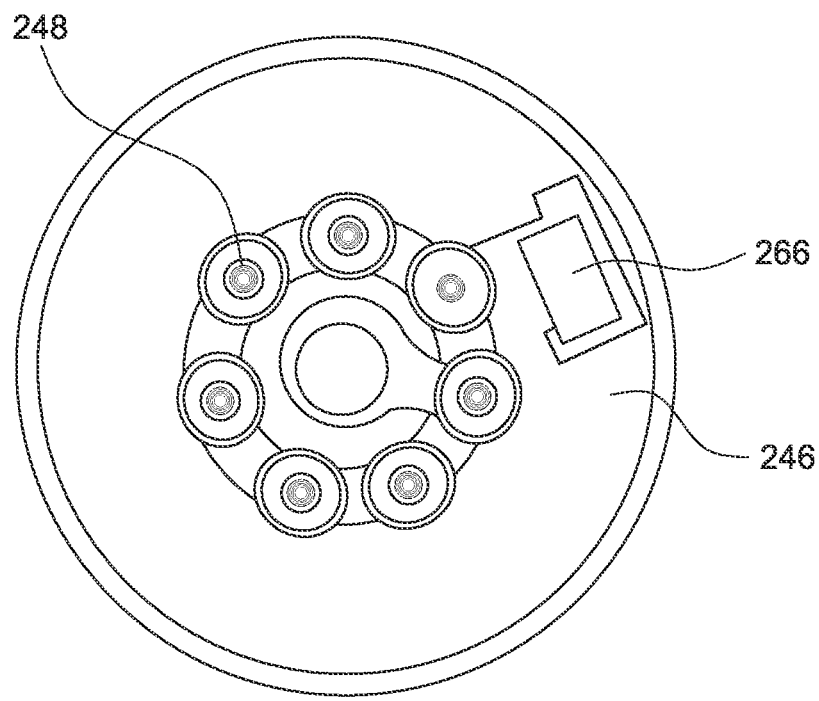
FIG. 12 shows an alternative embodiment of a circuit board in accordance with an embodiment of the present invention.
Figure 13:
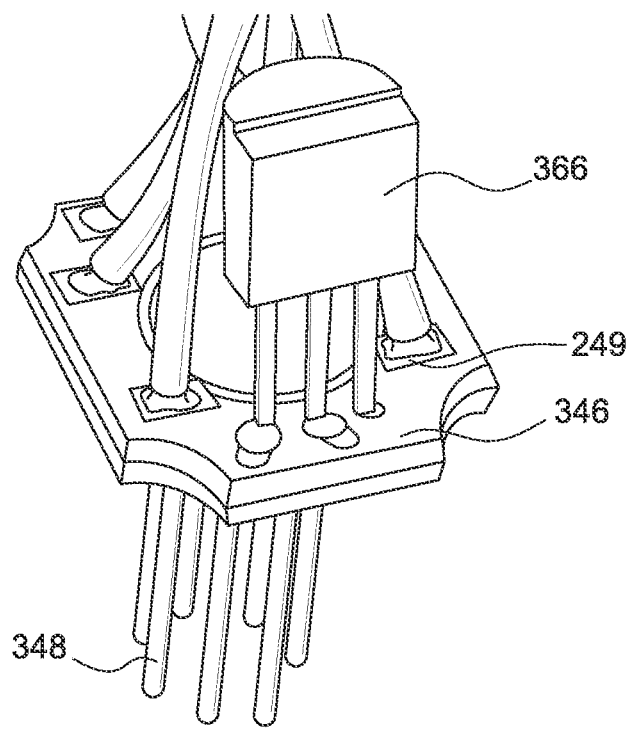
FIG. 13 shows an alternative embodiment of a circuit board in accordance with an embodiment of the present invention.

For example, FIG. 12 illustrates a circuit board 246 through which pins 248 extend. A flip chip style integrated circuit 266 is connected to the circuit board. The chip is connected between pins 248 such that information, including time of use information, stored on the chip 266 may be read by the control circuitry of the generator. FIG. 13 illustrates a further embodiment in which a Joint Electron Device Engineering Council, Transistor Outline Package, Case Style 92 ("TO-92") style semiconductor package is used to provide the non-volatile memory. The TO-92 package 366 is attached by pins 249 soldered or otherwise adhered to a rearward surface of the circuit board 346. The TO-92 package is electrically connected with pins 348 that extend from a forward surface of the circuit board in order to connect with a generator. As with the flip chip (266) described with respect to FIG. 12, the TO-92 package 366 is used to store information, including time of use information, so that it may be read by the control circuitry of the generator.

Figure 14:
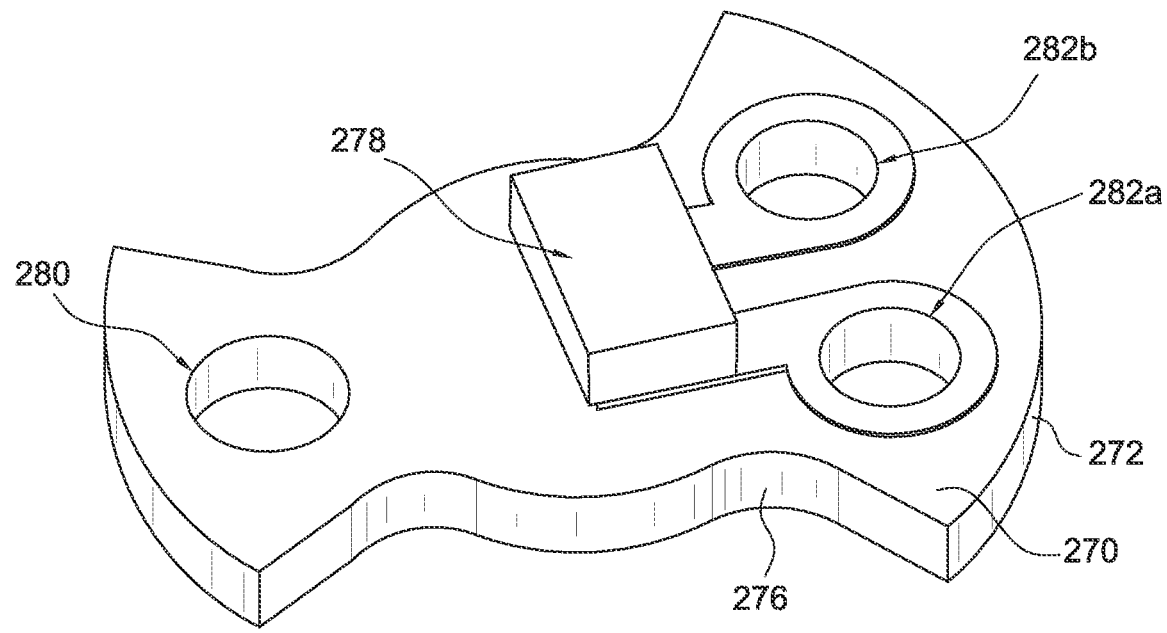
FIG. 14 shows an embodiment of a supplemental circuit board in accordance with embodiments of the invention.

In accordance with embodiments of the invention, as illustrated in FIG. 14, a supplemental circuit board 270 is provided. The supplemental circuit board 270 has a periphery 272 that generally matches the geometry of the inside edge 74 of the forward part of the shield 54. The supplemental circuit board 270 also includes one or more cutout portions 276. These cutouts allow for removal of the circuit board as will be discussed below. The supplemental circuit board carries non-volatile memory, which may be a flip chip 278 or other appropriate packaging for non-volatile memory. The supplemental circuit board also includes holes 280 in the circuit board that allow the pins 48 to pass through. The supplemental circuit board is inserted into the forward portion 54 of the shield 50 such that it sits at the base of the pins 48, adjacent to the dividing member 56 of the shield.

The holes 282*a*, 282*b* of the supplemental circuit board 270 that correspond to the pins that are connected by the semiconductor package 266, 366 on the circuit board 246, 346 are connected via the flip chip 278 on the supplemental circuit board. These holes 282*a*, 282*b* are sized such that they are biased to contact the pins with a friction fit and provide an electrical connection between the flip chip 270 and the pins. Alternatively, these pins could be soldered to contact patches formed on the circuit board.

Figure 15:
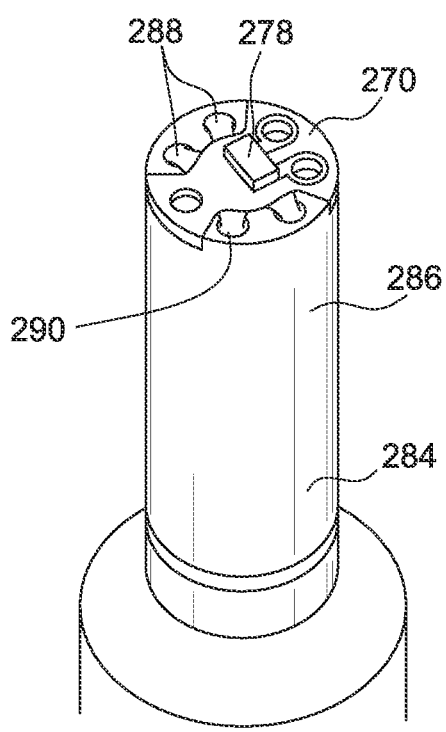
FIG. 15 shows an isometric view of an alternative embodiment of an installation tool in accordance with embodiments of the present invention.

The supplemental circuit board 270 is placed into the open end of the shield 54 and is pressed into position against the dividing member 56 using an installation tool 284, as illustrated in FIG. 15. The installation tool 284 has a plunger end 286 that includes holes 288 that correspond with the pins (248, 248) of the plug (40). The geometry of periphery of the plunger end matches the inside geometry of the plug shield open end (54). During repair or refurbishment of a powered medical device or wand, the supplemental circuit board 270 is placed on the top surface 290 of the plunger end 286 of the installation tool 284. The top surface of the installation tool may include a recessed portion that corresponds to the shape of the supplemental circuit board such that the circuit board fits on the installation tool in one orientation.

Figure 16:
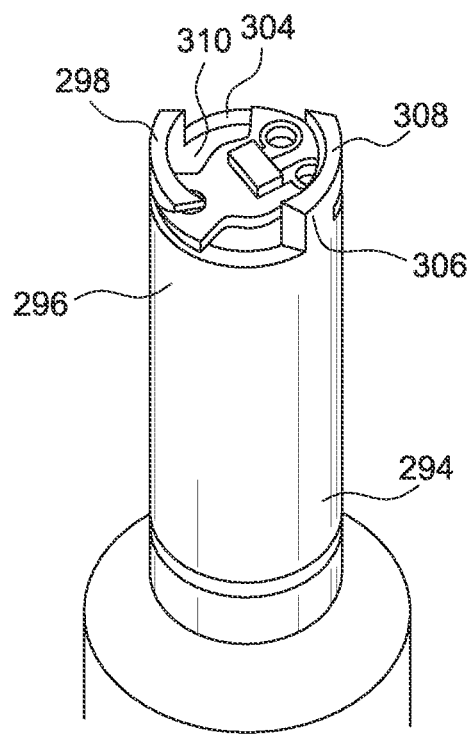
FIG. 16 shows an isometric view of an alternative embodiment of a removal tool in accordance with embodiments of the present invention.

In embodiments of the invention, the supplemental circuit board 270 may be removed and replaced with a second supplemental circuit board so that the wand may be repaired or refurbished more than once. The supplemental circuit board includes cutout sections 276 along a periphery 272 of the board. These cutouts 276 extend at least some distance into the surface of the board 270. As shown in FIG. 16, a removal tool is provided. The removal tool 294 includes a forward section 296 that is smaller in diameter than the inside of the forward portion of the shield (54). Prongs 298 extend from a top surface 304 of the removal tool. The prongs consist of a base section 306 that extends upward from the top surface of the removal tool and an engagement section or finger 308 that extends laterally from the base section.

To remove a supplemental circuit board 270 from a plug (40), the removal tool is inserted into the open end 54 of the plug such that the prongs 304 align with the cutouts 276 in the circuit board. The removal tool is then twisted such that the engagement portion 308 of the prongs 304 slides beneath a bottom surface of the circuit board 270 as shown in FIG. 16. The removal tool may then be pulled away from the plug, thereby removing the supplemental circuit board. The removal tool 296 may include a hollow interior portion 310 that surrounds the pins (248, 348) and allows the removal tool to be inserted and rotate without interfering with the pins.

Figure 17:
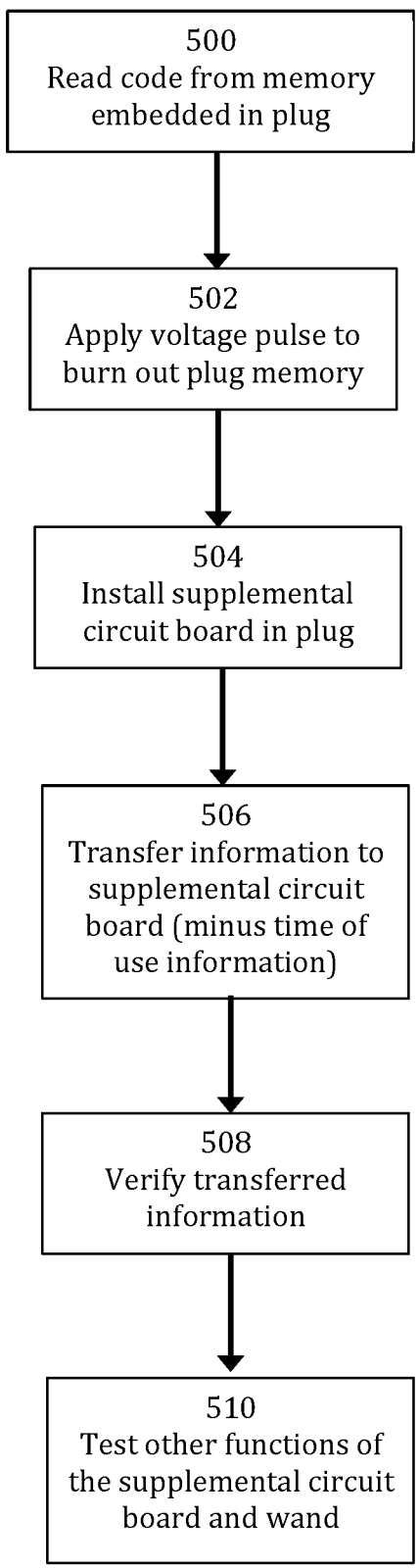
FIG. 17 shows a flow chart of the steps for refurbishing an electrosurgical instrument for the first time in accordance with embodiments of the present invention.

Programming and installing the supplemental circuit board 270 with the flip chip 278 such that the memory of the flip chip can be used appropriately and contains the appropriate information, including time of use information requires a number of steps. FIG. 17 shows a flow chart of the steps for refurbishing the wand a first time. First, information included on the memory contained within the plug is read 500 from the plug memory into an external device such as a computer or other controller where the data is stored in non-volatile memory. Next, a voltage pulse is applied to the memory device within the plug to burn out or destroy the functionality of the memory device 502. In the following step 504, the supplemental circuit board is installed in the plug. Next, the information recovered from the plug memory is transferred to the memory device of the supplemental circuit board 506.

In an alternative embodiment, the information may be transferred to the memory device of the supplemental circuit board prior to installation of the supplemental circuit board in the plug. In a further alternative, the necessary information for each model of medical device could be obtained at a prior time and stored in a database. The information could then be retrieved from the database for transfer to the memory device of the supplemental circuit board as needed. However, the information regarding time of use is not transferred to the memory of the supplemental circuit board, only information required by the generator as contained in a brand new device is burned into the chip. Following this step, the information transferred to the supplemental circuit board is verified 508 and, finally, all other functions of the supplemental circuit board and wand are tested 510. Other refurbishment or repair operations may be conducted on the wand or other powered medical device in order to prepare it for use.

Figure 18:
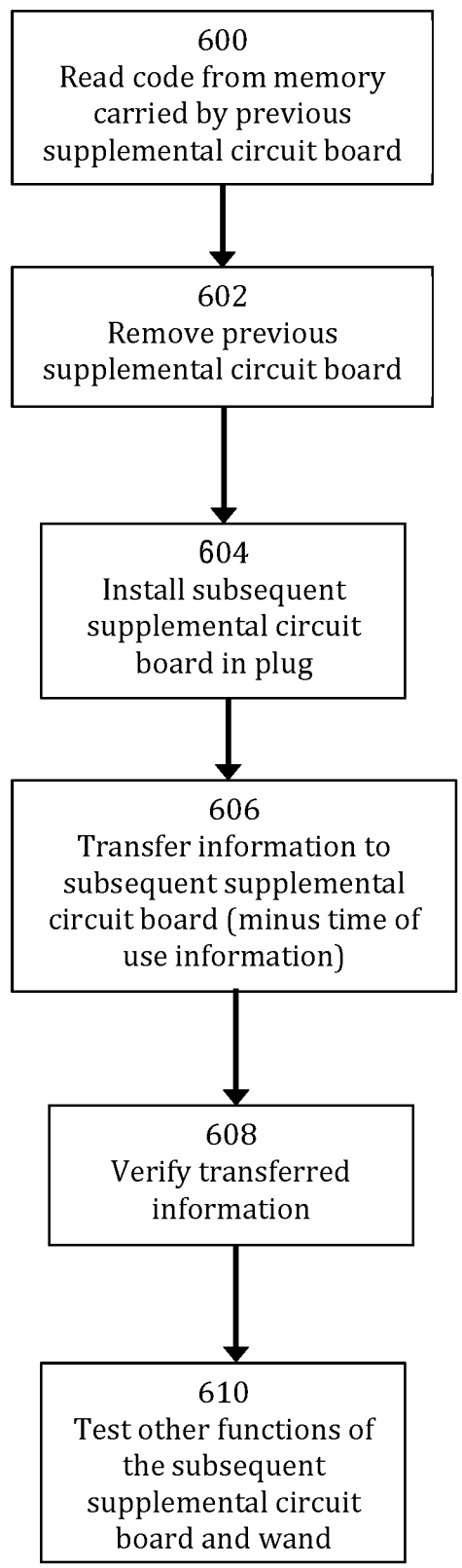
FIG. 18 shows a flow chart of the steps for refurbishing an electrosurgical instrument for a second or subsequent time in accordance with embodiments of the present invention.

FIG. 18 shows a flow chart of the steps for refurbishing the wand a second or subsequent time, after a supplemental circuit board has already been installed. First, the data included on the memory contained within the previously installed supplemental circuit board is read 600 from the circuit board memory into an external device such as a computer or other controller where the data is stored in non-volatile memory. Next, the previous supplemental circuit board is removed from the plug 602. In the following step 604, the subsequent supplemental circuit board is installed in the plug. Next, the information recovered from the previous supplemental circuit board memory is transferred to the memory device of the subsequent supplemental circuit board 606. However, the information regarding time of use is not transferred to the memory of the subsequent supplemental circuit board, only information required by the generator as contained in a brand new device is burned into the chip. Following this step, the information transferred to the subsequent supplemental circuit board is verified 508 and, finally, all other functions of the subsequent supplemental circuit board and wand are tested 510. Again, other refurbishment or repair operations may be conducted on the wand or other powered medical device in order to prepare it for use. As discussed with regard to a first refurbishment, the information may be transferred to the memory device of the supplemental circuit board prior to installation of the supplemental circuit board in the plug, and the necessary information for each model of medical device could be obtained at a prior time, stored in a database, and retrieved from the database for transfer to the memory device of the supplemental circuit board as needed.

The flip chip 278 of the supplemental circuit board is functionally equivalent to the memory device 266, 366 of the circuit board 246, 346. This means that the flip chip 278 functions in a sufficiently similar manner such that the powered medical device is capable of functioning with the flip chip 278 used in place of the memory device 266, 366. In this manner, a memory device that is disabled, expended, consumed, damaged or otherwise rendered inoperable as part of the time limiting function of the powered medical device may be replaced without the need to replace the entire plug or damage the integrity of the plug by destroying a plug component to gain access to the fuse.

Various embodiments discussed above reference a flip chip. However, one of ordinary skill in the art would recognize that any appropriate memory device capable of meeting the size constraints of the plug could be used.

In addition, various embodiments discuss the use of a supplemental circuit board. As used herein, supplemental circuit board is not limited to any particular structure or composition. Rather, this term may include any structure that provides for electrical connection of one or more electronic components to the pins of a plug or other accessible electrical elements of a powered medical device. The supplemental circuit board may be any size or shape that allows it to bridge between pins of the plug, and it need not match the geometry of the plug. For example, in certain embodiments, the supplemental circuit board may comprise a printed circuit board with conductive tracks laminated onto a non-conductive substrate to which electronic components are attached. In other embodiments, the supplemental circuit board may comprise a molded structure in which electronic components are embedded.

In further embodiments, the supplemental circuit board need not be a circuit board in the sense of requiring a non-conductive substrate with components mounted on its surface. The supplemental circuit board may have any configuration that comprises one or more electronic components coupled with means to connect the electronic component to pins or other connectors of the plug. For example, the supplemental circuit board may comprise a memory chip (such as an EPROM or EEPROM), a fuse or another electronic component that is coupled with ring connections that slide onto pins of the plug.

The powered medical devices and methods have been described as having certain exemplary features or steps. However, it is contemplated that the present invention may include any compatible features or steps shown or describe with respect to other embodiments disclosed herein or other features as would be understood by one of ordinary skill in the art.

What is claimed is:

1. A medical device comprising:
a plug adapted to connect the medical device to a device controller, the plug comprising a connector;
a first electronic component electrically connected with the connector, the first electronic component having previously been adapted to perform a first function when the medical device is connected to an external device a first time and having been disabled from performing the first function when the medical device is connected to the external device a subsequent time; and
a second electronic component adapted to perform the first function and electrically connected with the connector.

2. The medical device of claim 1, wherein the first electronic component comprises a first fuse.

3. The medical device of claim 2, wherein the first electronic component has been disabled by burning the fuse.

4. The medical device of claim 3, wherein the second electronic component comprises a second fuse.

5. The medical device of claim 4, wherein the second fuse is electrically equivalent to the first fuse prior to the first fuse being burned.

6. The medical device of claim 4, wherein the second fuse is sufficiently electrically equivalent to the first fuse prior to the first fuse being burned such that the medical device functions in the same manner when the second fuse is used in place of the first fuse.

7. The medical device of claim 1, wherein the first electronic component comprises non-volatile memory.

8. The medical device of claim 7, wherein the second electronic component comprises non-volatile memory.

9. The medical device of claim 1, wherein the medical device comprises an electrically powered medical device.

10. The medical device of claim 1, wherein the first electronic component is embedded in the medical device.

11. The medical device of claim 1, wherein the first electronic component is embedded in the plug.

12. The medical device of claim 1, wherein the second electronic component is inserted into the plug.

13. The medical device of claim 1, the second electronic component performing the first function when the medical device is connected to the external device the subsequent time.

14. The medical device of claim 1, wherein the external device comprises a power supply.

15. The medical device of claim 1, wherein the second electronic component is not connected with the connector when the medical device is connected to the external device the first time.

16. The medical device of claim 15, wherein the second electronic component is connected with the connector after the medical device is connected to the external device the first time.

17. The medical device of claim 1, wherein the second electronic component is connected with the connector when the medical device is connected to the external device the subsequent time.

18. The medical device of claim 1, wherein the second electronic component is functionally equivalent to a non-disabled first electronic component.

19. The medical device of claim 1, wherein the second electronic component functions in a sufficiently similar manner to a non-disabled first electronic component such that the medical device functions with the second electronic component used in place of the first electronic component.

* * * * *